United States Patent [19]

Maxon

[11] Patent Number: 4,849,127
[45] Date of Patent: Jul. 18, 1989

[54] DIMETHICONE COPOLYOL SULFOSUCCINATES

[75] Inventor: Bartley D. Maxon, Cicero, Ill.

[73] Assignee: McIntyre Chemical Company, Chicago, Ill.

[21] Appl. No.: 99,777

[22] Filed: Sep. 22, 1987

Related U.S. Application Data

[62] Division of Ser. No. 479, Jan. 5, 1987, Pat. No. 4,717,498.

[51] Int. Cl.[4] .......................... C11D 1/04; C11D 1/12; C11D 9/36
[52] U.S. Cl. .......................... 252/174.15; 252/174.18; 252/174.21; 252/174.22; 252/557; 252/DIG. 4; 252/DIG. 5; 252/DIG. 13; 556/428; 556/437
[58] Field of Search .............................. 556/428, 437; 252/174.15, 174.18, 538, 557, 174.21, 174.22, DIG. 4, DIG. 5, DIG. 13

[56] References Cited

U.S. PATENT DOCUMENTS

| | | | |
|---|---|---|---|
| 3,427,271 | 2/1969 | McKellar | 556/437 |
| 3,637,783 | 1/1972 | Haluska | 556/437 |
| 4,248,590 | 2/1981 | Koerner et al. | 556/428 |
| 4,658,049 | 4/1987 | Nakano et al. | 556/437 |

Primary Examiner—Paul Lieberman
Assistant Examiner—Hoa Van Le
Attorney, Agent, or Firm—Niro, Scavone, Haller, Niro & Rockey, Ltd.

[57] ABSTRACT

Dimethicone copolyol sulfosuccinate compounds obtained from silicone-based monoesters. The dimethicone copolyol sulfosuccinates are obtained by reacting the ethoxylated polyether side chains of dimethicone copolyol with maleic anhydride to form a monoester and then converting the monoester to a sulfosuccinate by sulfonation of the double bond with a metallic sulfite, an amine or with a combination of a metallic sulfite and an amine. Dimethicone copolyol sulfosuccinates are silicone-based compounds which are useful as surfactants for improving the mildness and foam enhancing and stabilizing properties of shampoos and other personal care products.

28 Claims, 2 Drawing Sheets

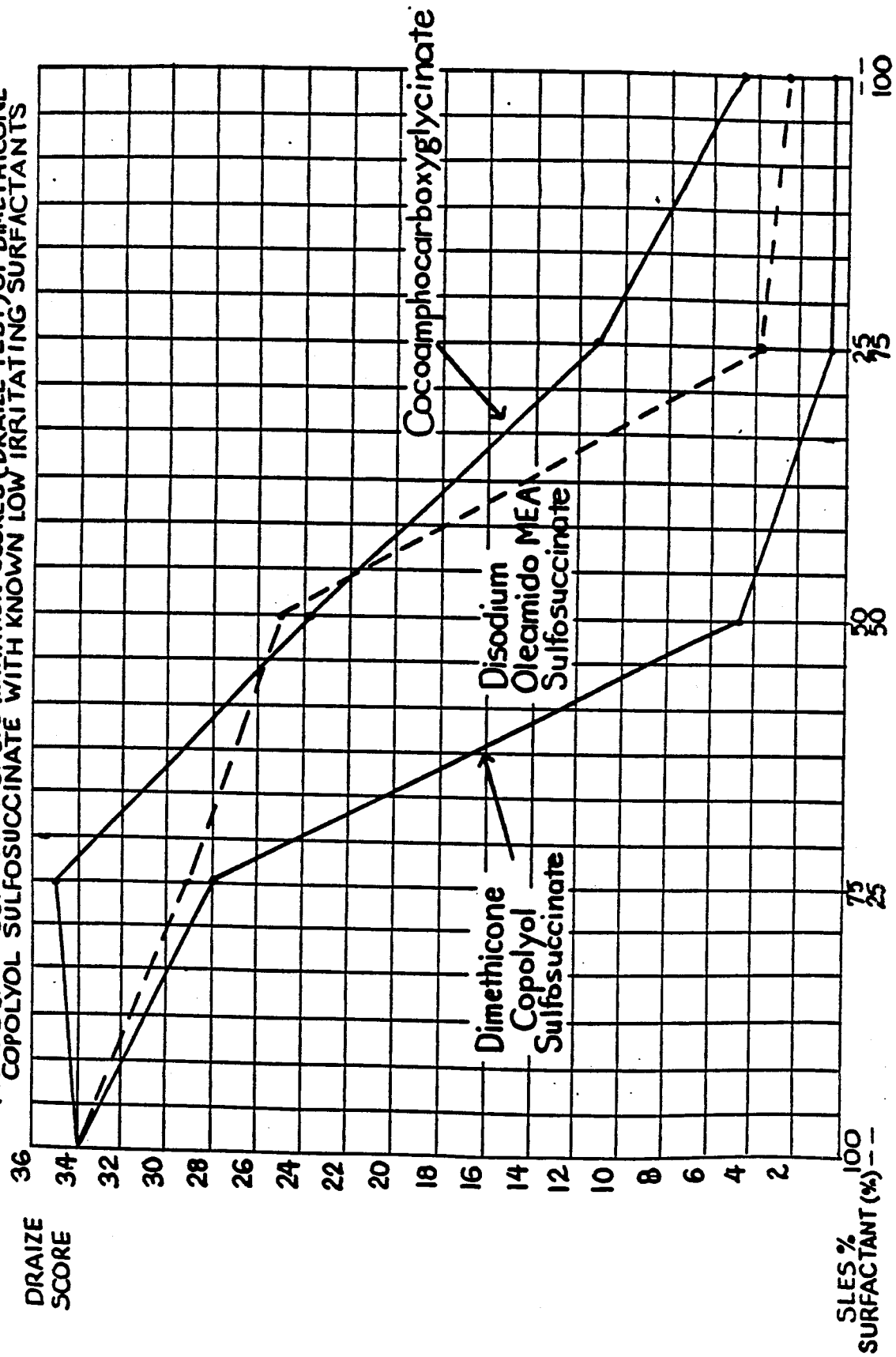

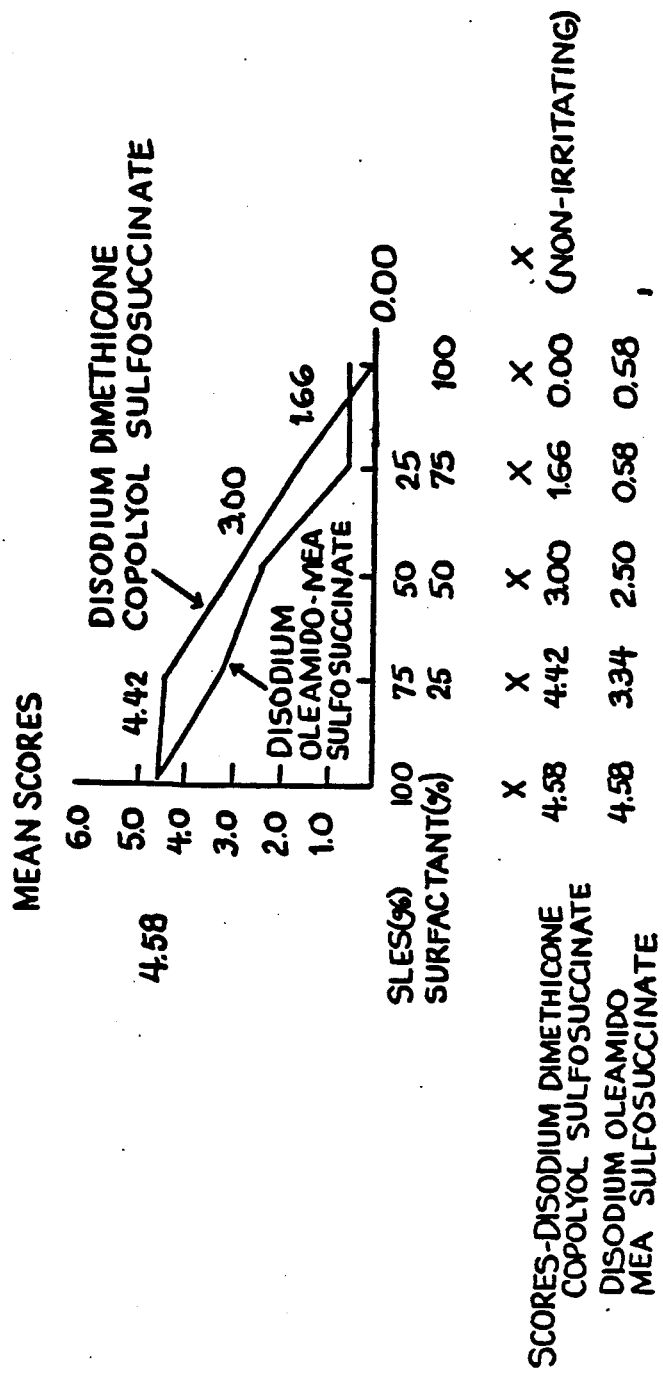

DIMETHICONE COPOLYOL SULFOSUCCINATES

This is a division of co-pending application Ser. No. 000,479, filed on Jan. 5, 1987, now U.S. Pat. No. 4,717,498.

BACKGROUND OF THE INVENTION

The present invention relates to dimethicone copolyol sulfosuccinates. More specifically, the invention relates to silicone-based sulfosuccinates that exhibit increased mildness and foaming properties when used as surfactants in shampoos and other personal care products.

Sulfosuccinate surfactants have been used in the cosmetic industry primarily to improve the mildness of shampoos and other personal care products. Such surfactants are usually diesters or monoesters, with the monoester being preferred because of its mildness and foam enhancement properties. Heretofore, primarily two half ester or monoester derivatives have been used for shampoos which include derivatives of monoalcohol amides, such as oleamide MEA, oleamide IPA and undecylenamide MEA, and derivatives of fatty alcohols and ethoxylated alcohols, such as lauryl, laureth and oleyl alcohols.

The sulfosuccinates obtained from diesters and monoesters vary considerably in their foaming, viscosity building, solubility and conditioning properties. In general, they are gentle to the skin and eyes when compared to high foaming surfactants, and are usually blended with such high foaming surfactants to obtain surfactants which exhibit some degree of both mildness and foaming properties.

While some sulfosuccinate surfactants having mildness and foaming properties useful in the industry have been known and used, the preparation of such surfactants from certain ester derivatives containing silicone has not been accomplished. The present invention is directed generally to sulfosuccinate surfactants derived from silicone-based esters which demonstrate improved mildness, foam enhancing and stabilizing properties over known surfactants.

SUMMARY OF THE INVENTION

The present invention relates generally to compositions of dimethicone copolyol sulfosuccinates of the formula:

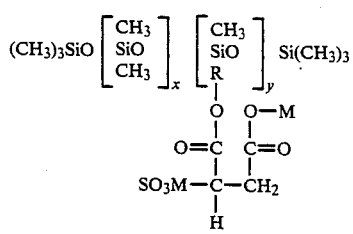

wherein R is a polymer or copolymer of ethylene or propylene oxide, M is an alkali (Group I A) metal, for example, sodium, potassium or lithium, or ammonium group, and x and y range in value so as to produce a compound with an equivalent weight between 700 and 1600 grams. R may be further defined as a polymer or copolymer of ethylene or propylene oxide in the following forms:

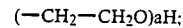

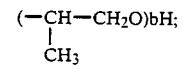

wherein a and b range in value from 1 to 30;

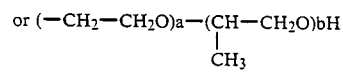

wherein a and b may range in value from 0 to 30.

A variation of the composition of the present invention is represented by the formula:

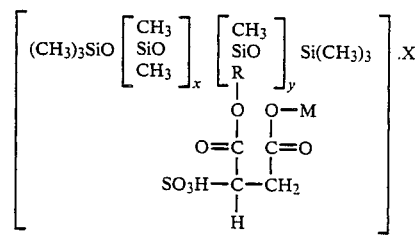

wherein X is an amine group obtained from alcohol amines, ethoxylates or propoxylates, preferably derived from the group consisting of monoethanolamine, diethanolamine, triethanolamine, monosopropanolamine or diglycolamine.

An even further variation of the composition of the present invention is represented by the formula:

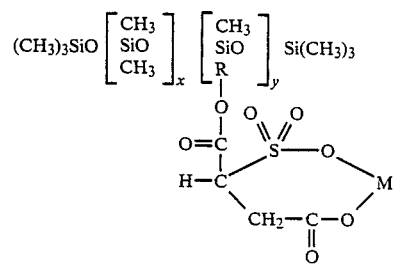

wherein M' is an alkaline (Group II) metal, for example, calcium, maganesium or barium, rather than an alkali metal.

Another form of the composition of the present invention is represented by the following formula:

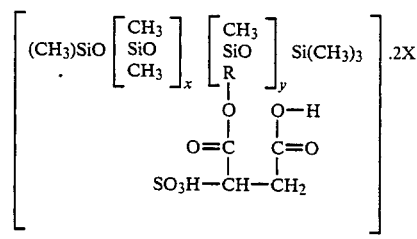

wherein X is an amine group as described above and obtained from sulfite salts containing said amine group.

The compositions of the present invention are generally prepared by reacting the ethoxylated polyether side chains of dimethicone copolyol with maleic anhydride to form a monoester and then converting the monoester to a sulfosuccinate by sulfonation of the double bond with a metallic sulfite. Metallic sulfite and amine salts may also be used either alone or in combination for sulfonation of the double bond. The resulting sulfosuccinate is a silicone-based surfactant which exhibits highly improved mildness and foam stabilizing properties.

It is, an object of the present invention therefore, to prepare novel dimethicone copolyol sulfosuccinates having silicone-based compositions.

It is a further object of this invention to prepare improved dimethicone copolyol sulfosuccinates with metallic, ammonium or amine constituents.

Further objects of this invention are to prepare novel dimethicone copolyol sulfosuccinates which can be used as surfactants in shampoo and other personal care products and to provide novel surfactants which exhibit improved mildness and foam stabilizing properties.

These and other objects of the present invention together with the advantages thereof will become apparent to those skilled in the art from the detailed disclosure of preferred embodiments of the present invention as set forth below.

DETAILED DESCRIPTION OF THE PREFERRED EMBODIMENTS OF THE INVENTION

The dimethicone copolyol sulfosuccinate compositions of the present invention generally are prepared by reacting the ethoxylated polyether side chains of dimethicone copolyol with maleic anhydride to form a monoester. The side chains involved in this reaction are polymers or copolymers of ethylene or propylene oxide. The condensation reaction with maleic anhydride is represented by the following:

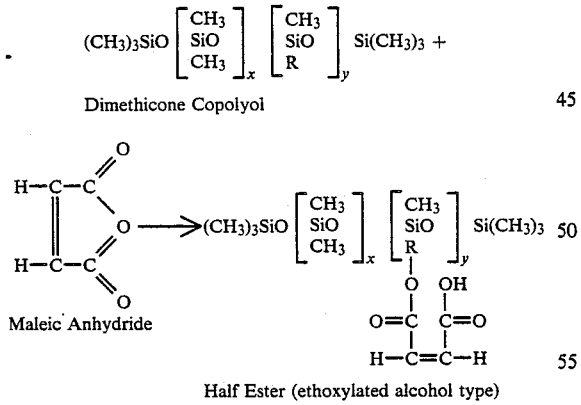

Half Ester (ethoxylated alcohol type)

In the above equation, R is a polymer or copolymer of ethylene or propylene oxide, with the preferred composition selected from the following formulas:

$(-CH_2-CH_2O)_aH$;

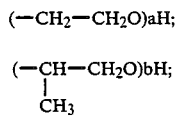

wherein a and b range in value from 1 to 30;

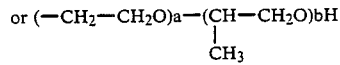

wherein a and b may range in value from 0 to 30. The values of x and y are intended to produce a final product with an equivalent weight between 700 and 1600 grams. The ratio of x and y to R ranges in value from 1.5:1 to 15.3:1, with the preferred ratio in the range of 10:1 to 15.3:1.

The preferred condensation reaction proceeds by reacting 1.00 moles of dimethicone copolyol with 1.0 to 1.30 moles of maleic anhydride. The dimethicone copolyol is heated to a temperature of 60°-100° C., with the preferred temperature ranging between 70°-90° C. The maleic anhydride is completely dissolved and dispersed and the reaction product, the maleic monoester of dimethicone copolyol, is then maintained at a temperature of 60°-100° C., preferably between 70°-90° C., under conditions and according to practices known to those skilled in the art until a constant acid value or number is obtained.

The maleic monoester of dimethicone copolyol is then converted into the composition of the present invention by sulfonating the double bond with either a metallic or ammonium sulfite, an amine sulfite or a combination of a metallic or ammonium sulfite and an amine. The preferred conversion is accomlished by reacting the maleic anhydride portion of the dimethicone copolyol monoester with equal moles of the metallic sulfite in an aqueous solution in the following manner:

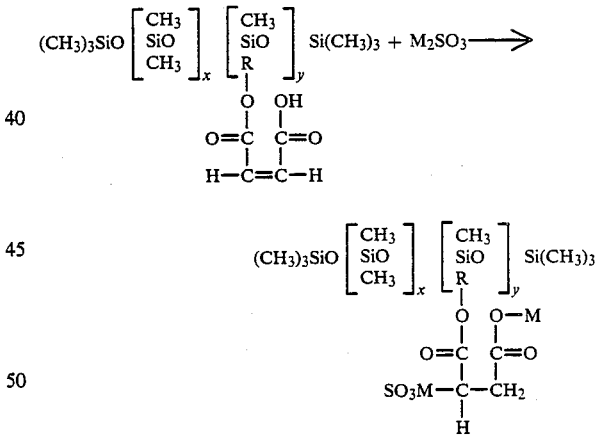

where M is an alkali (Group IA) metal, for example, sodium, potassium or lithium, or ammonium group.

The metallic sulfite is dissolved in water at a temperature of about 40° to 95° C., preferably between about 50° to 70° C. After the metallic sulfite is thoroughly dissolved, the maleic monoester of dimethicone copolyol is added to the solution, with the reaction product maintained in a fluid state. The product is allowed to react for approximately one half hour to three hours, until the conentration of the free metallic sulfite is between about 0 and 3%, with the preferred concentration less than about 2%.

In another embodiment, the conversion of the maleic monoester of dimethicone copolyol to a sulfosuccinate can be accomplished by using compounds other than or in addition to alkali metal or ammonium sulfites. Specifically, the alkali metal or ammonium sulfites, in conjunction with an amine, can be used to sulfonate the double bond of the monoester. These sulfosuccinates, can be prepared in the following manner:

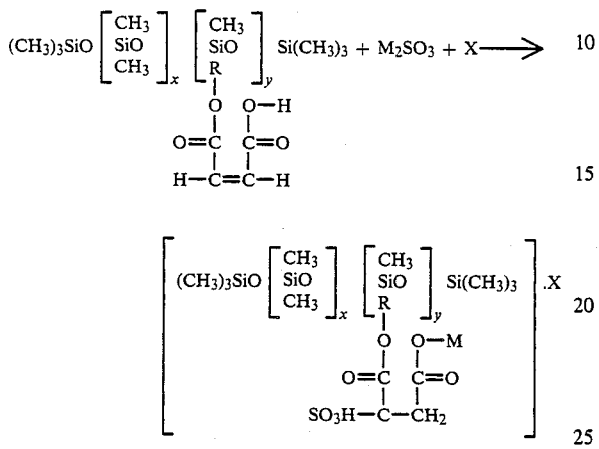

wherein M is an alkali metal or ammonium group and X is an amine group obtained from alcohol amines, ethoxylates or propoxylates, preferably derived from the group consisting essentially of monoethanolamine, diethanolamine, triethanolamine, monoisopropanolamine and diglycolamine.

Alkaline sulfites can also be used in place of alkali metal or ammonium sulfites to convert the maleic monoester of dimethicone copolyol to a sulfosuccinate. When used alone, the conversion reaction occurs in the following manner:

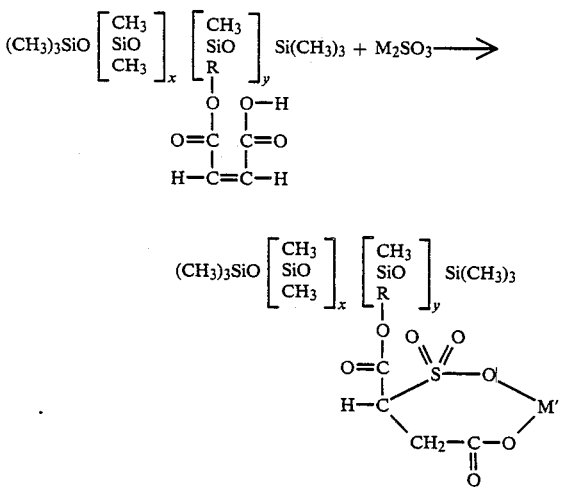

wherein M' is an alkaline (Group II) metal, for example, calcium, magnesium or barium.

Amine sulfites can also be used without the metallic sulfites to convert the maleic monoester of dimethicone copolyol to a sulfosuccinate. When used alone, the conversion reaction occurs as follows:

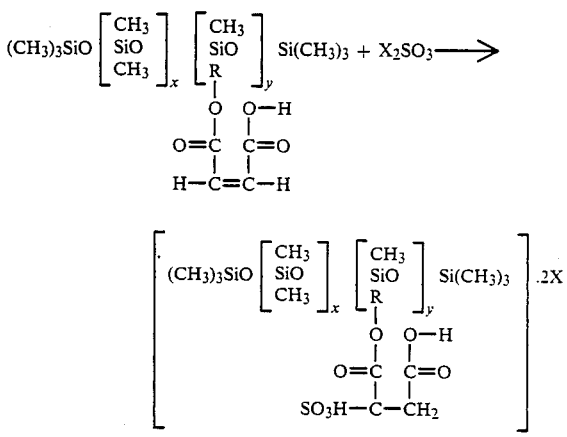

wherein X is an amine group obtained from alcohol amines, ethoxylates or propoxylates, preferably from the groups consisting essentially of monoethanolamine, diethanolamine, triethanolamine, monoisopropanolamine or diglycolamine.

In regard to the values for x and y in the dimethicone copolyol compounds used to produce the compound of the present invention, actual values cannot be readily determined because such values are trade secrets and not released or made public by the commercial manufacturers of dimethicone copolyol. For example, one of the dimethicone copolyol compounds actually used and contemplated for the reaction by the present inventor is manufactured by the Dow Corning Corporation under the label Dow Corning® 190 and 193 Surfactant. Other sources of dimethicone copolyol compounds include Union Carbide Corporation, Goldschmidt and Mazer Chemicals, Inc. However, information regarding these compounds is published in very general terms (e.g., relative molecular weight and ratio of the values of x and y to R) with the actual value of x and y, or molecular weight, maintained as a trade secret.

It has been determined by the inventor that the preferred type of dimethicone copolyol compounds used to prepare the compound of the present invention should desirably possess the following characteristics: the compound should have an equivalent weight in the range of about 500 to 1100 grams and should be essentially free from any extraneous solvents. If the equivalent weight of the dimethicone copolyol is too high, the amount of the other reactants (maleic anhydride and bisulfite compounds) will be insufficient to react properly, and the resulting product will have either slight or no differences in properties from the original dimethicone copolyol. If extraneous solvents are present in too large amounts, such solvents interfere with the reaction to the extent that no reaction can occur or the reaction can be partially blocked. The resulting product then will not possess the desired characteristics of an improved surfactant.

The value of x and y are further defined by reference to certain characteristics of the dimethicone copolyol sulfosuccinates contemplated in the present invention. The equivalent weight of the compound should range from about 700 grams to 1600 grams, with HLB (hydrophilic/lipophilic balance) values ranging from about 1.5:1 to 15.3:1, preferrably ranging from about 10:1 to 15.3:1. The hydrophilic/lipophilic balance represents a ratio of the silicone portion of the compound, the x and y values, to the ethoxylated side chain portion of the compound, and R value. When the hydrophilic/lipophilic balance falls below the range of HLB values set forth, the clarity and foam performance of the sulfosuccinate decreases. When the HLB balance exceeds the preferred range, the sulfosuccinate does not exhibit all the desired characteristics of an improved surfactant.

Diester dimethicone copolyol sulfosuccinates can also be prepared using this two-stage process by reacting 2 moles of the diester with 1 mole of the metallic bisulfite or amine bisulfite.

Several tests have been conducted using some representative compositions of the present invention, including disodium dimethicone copolyol sulfosuccinate, dipotassium dimethicone copolyol sulfosuccinate, diammonium dimethicone copolyol sulfosuccinate and the triethanolamine dimethicone copolyol sulfosuccinate to determine whether some of the compositions of the present invention exhibit improved mildness and foam stabilizing properties.

Each composition was prepared using the process described earlier by which 1.00 mole of dimethicone copolyol was reacted with 1.0 to 1.3 moles of maleic anhydride. For example, disodium dimethicone copolyol sulfosuccinate and dipotassium dimethicone copolyol sulfosuccinate were prepared in the following manner. One mole of the dimethicone copolyol was heated to a temperature between about 80°–90° C., then 1.3 moles of the maleic anhydride was completely dissolved and dispersed throughout the dimethicone copolyol. The mixture was then maintained at a temperature between about 80°–90° C. for a length of time to allow the reaction to proceed and until the reaction product reached a substantially constant acid value.

The reaction product, the maleic monoester of dimethicone copolyol was then reacted with sodium sulfite in one instance, and potassium in the other, in the following manner. One mole of each sulfite was thoroughly dissolved in water at a temperature between about 65°–70° C. and the maleic monoester of dimethicone copolyol was slowly added to the solution. The resulting mixture was allowed to react for approximately one half hour to three hours, until the concentration of the free sulfite compound was less than 2%. Samples of diammonium dimethicone copolyol sulfosuccinate and triethanolomine dimethicone copolyol sulfosuccinate were also prepared using this same procedure.

One series of tests using the compositions described above, measured the mildness properties of the compositions of the present invention using the rabbit eye irritation method. Albino rabbits of the New Zealand strain were used as test animals, and the test sample was instilled into the right eye of each rabbit in accordance with the procedure listed in the Table of Eye Irritation Results under Form Administered, with the left eye serving as the control. The Draize Method was used for evaluation, and at each scoring interval the cornea, iris and palpebral conjunctivae were examined and graded for irritation and injury in accordance with the Draize scoring systems. A rating was obtained by selecting the maximum mean irritation score at 1, 24, 48 or 72 hours after instillation of the sample. The descriptive rating system for the mean irritation score is shown in Table 1:

TABLE 1

EYE IRRITATION TEST DESCRIPTIVE RATING SYSTEM

| Classification | Range | Definition |
|---|---|---|
| Non-irritating | 0.0–0.5 | To maintain this rating, all scores at 24-hour readings must be zero; otherwise, increase rating one level. |
| Practically Non-irritating | Greater than 0.5–2.5 | To maintain this rating, all scores at the 24-hour reading must be zero; otherwise, increase rating one level. |
| Minimally Irritating | Greater than 2.5–15.0 | To maintain this rating, all scores at the 72-hour reading must be zero; otherwise, increase rating one level. |
| Mildly Irritating | Greater than 15.0–25.0 | To maintain this rating, all scores at the 7-day reading must be zero; otherwise, increase rating one level. |
| Moderately Irritating | Greater than 25.0–50.0 | To maintain this rating, scores at 7 days must be less than or equal to 10 for 60% or more of the animals. Also, mean 7-day score must be less than or equal to 20. If the 7-day mean score is less than or equal to 20 but less than 10, then no animal among those showing scores greater than 10 can exceed a score of 30 if rating is to be maintained; otherwise, increase rating one level. |
| Severely Irritating | Greater than 50.0–80.0 | To maintain this rating, scores at 7 days must be less than or equal to 30 for 60% or more of the animals. Also, mean 7-day score must be less than or equal to 40. If 7-day mean score is less than or equal to 40, but less than or equal to 30, then no animal among those showing scores greater than 30 can exceed a score of 60 if rating is to be maintained; otherwise, increase rating one level. |
| Extremely Irritating | Greater than 80.0–110.0 | |

Solutions of disodium dimethicone copolyol sulfosuccinate, a composition of the present invention, sodium laureth-3 sulfate (SLES) and blends of disodium dimethicone copolyol sulfosuccinate with sodium laureth-3 sulfate were prepared and used in the eye irritation tests. Sodium laureth-3 (SLES) sulfate is a relatively irritating high foaming surfactant commonly used in commercial products, and was used for comparison purposes to demonstrate the mildness properties of the sulfosuccinate surfactants. About 0.1 ml. of each solution was instilled in the right eye of the test rabbits, and the eye irritations were measured at 24-, 48-, and 72-hour intervals. The mean irritation values are recorded in Table 2:

TABLE 2

| Solution | Mean Irritation Score |
|---|---|
| Sodium Laureth-3 Sulfate (SLES - 15% active) | 34.0/110.0 |
| Disodium Dimethicone Copolyol Sulfosuccinate (15% active) | 0.7/110.0 |
| Disodium Dimethicone Copolyol Sulfosuccinate (40% active) | 3.3/110.0 |
| Blend #1 (15% active) 25% Disodium Dimethicone Copolyol Sulfosuccinate 75% SLES | 28.1/110.0 |
| Blend #2 (15% active) 50% Disodium Dimethicone Copolyol Sulfosuccinate 50% SLES | 4.7/110.0 |
| Blend #3 (15% active) 75% Disodium Dimethicone Copolyol Sulfosuccinate 25% SLES | 0.7/110.0 |

The test results demonstrate the mildness properties of the sulfosuccinate surfactants alone, as well as the effectiveness of the sulfosuccinate in a blend with a high foaming surfactant. The sulfosuccinate obtained ratings in the non-irritating to practically non-irritating range when tested alone, and was 90% milder than the commonly used SLES surfactant. Blends of disodium dimethicone copolyol sulfosuccinate and SLES decreased the irritation rating of SLES alone, and obtained practically non-irritating to minimally irritating ratings in blends #2 and #3.

Eye irritation tests were also conducted to determine the mildness properties of dipotassium, diammonium and triethanolamine dimethicone copolyol sulfosuccinates. The results of these tests, using 15% active solutions, are recorded in Table 2A:

TABLE 2A

| Solution | Mean Irritation Score |
| --- | --- |
| Sodium Laureth-3 Sulfate (SLES - 15% active) | 34.0/110.0 |
| Disodium Dimethicone Copolyol Sulfosuccinate (15% active) | 0.7/110.0 |
| Dipotassium Dimethicone Copolyol Sulfosuccinate (15% active) | 0.0/110.0 |
| Diammonium Dimethicone Copolyol Sulfosuccinate (15% active) | 1.3/110.0 |
| Triethanolamine Dimethicone Copolyol Sulfosuccinate (15% active) | 1.3/110.0 |

The values obtained for the sulfosuccinate surfactants demonstrate mildness properties within the practically non-irritating range for all the compounds tested. When these values are compared with the sodium laureth-3 sulfate value, the sulfosuccinate surfactants are over 96% milder than the SLES surfactant.

The eye irritation test results for disodium dimethicone copolyol were then compared with test results of two known surfactants cocoamphocarboxyglycinate and disodium oleamido MEA sulfosuccinate, widely used to improve the mildness and foaming stability of commercial products. Each surfactant was blended with sodium laureth-3 sulfate (SLES) in the following manner:

| SLES | 100% | 75 | 50 | 25 | — |
| --- | --- | --- | --- | --- | --- |
| Surfactant | — | 25 | 50 | 75 | 100 |

Eye irritation studies employing three rabbits were then conducted on each solution; and the mean irritation scores based on the Draize method were obtained. The scores are graphically represented in FIG. 1.

These results demonstrate a reduction in eye irritation from the disodium dimethicone copolyol sulfosuccinate at all levels in comparison to the two known mild surfactants, with a significant reduction at the 50/50 range of solutions. While the disodium dimethicone copolyol sulfosuccinate shows minimal irritation, the two known surfactants are classified as mild to moderately irritating. Such results are significant considering that one of the known surfactants, cocoamphocarboxyglycinate, is a surfactant generally used in baby shampoo formulations, where mildness is essential.

A skin irritation test was performed using the primary skin irritation method (FHSA) in a patch test technique on three male albino rabbits. The hair was clipped from the abdomen of the rabbits and 4 areas approximately ten centimeters apart, were designated for application of the patches. Two one-square inch sights on the right side of the abdomen were abraded while similar sites on the left side remained unabraded.

Test samples (0.5 milliliters) of dimethicone copolyol sulfosuccinate and disodium oleamido-MEA sulfosuccinate were placed on the skin of the rabbits under a one-inch square piece of cotton gauze which was held in place with adhesive tape. The entire trunk of the animal was then wrapped with a rubberized cloth and remained for a 24 hour exposure period. After 24 hours the patches were removed and the skin was examined for signs or irritation (erythema and/or edema). The skin was examined again at the end of 72 hours. The descriptive rating system for mean irritation scores is shown in Table 4:

TABLE 4

| PRIMARY SKIN IRRITATION TEST DESCRIPTIVE RATING SYSTEM | |
| --- | --- |
| | Value* |
| A. Erythema and Eschar Formation | |
| Very slight erythema (barely perceptible) | 1 |
| Well defined erythema | 2 |
| Moderate to severe erythema | 3 |
| Severe erythema (beet redness) to slight eschar formation (injuries in depth) | 4 |
| B. Edema Formation | |
| Very slight edema (barely perceptible) | 1 |
| Slight Edema (edges of area well defined by definite raising) | 2 |
| Moderate edema (area raised approx. 1 mm) | 3 |
| Severe edema (raised more than 1 mm and extending beyond area of exposure) | 4 |

*The value recorded for each reading is the average value of the animals subject to the test.

The average values for erythema and eschar formation at 24 hours and 72 hours for intact skin were added to values for abraded skin at 24 and 72 hours (4 values). Similarly, values for edema formation at 24 and 72 hours for intact and abraded skin were added (4 values). The total of the 8 values was divided by 4 to obtain the primary irritation score. A primary skin irritant is a substance which results in an empirical primary irritation score of 5 or more.

Each surfactant was blended with sodium laureth-3 sulfate (SLES) in the following manner:

| SLES | 100% | 75 | 50 | 25 | — |
| --- | --- | --- | --- | --- | --- |
| Surfactant | — | 25 | 50 | 75 | 100 |

The mean irritation scores were determined and the results are graphically represented in FIG. 2.

The results of the skin irritation test demonstrate that the disodium dimethicone copolyol sulfosuccinate is relatively mild when compared with a known low-irritating surfactant under similar conditions. While the results are not as dramatic as those from the eye irritation tests, a definite reduction in irritation scores comparable to that of the known surfactant is obtained, with a non-irritating value for dimethicone copolyol sulfosuccinate at 100% concentration.

Other tests were conducted to evaluate the foaming stabilizing and enhancing properties of the composition of the present invention. Disodium dimethicone copolyol sulfosuccinate was blended with sodium laureth-3 sulfate (SLES), a high foaming surfactant in the following active ratios:

|   | A | B | C | D | E |
|---|---|---|---|---|---|
| SLES | 100% | 75 | 50 | 25 | — |
| Disodium Dimethicone Copolyol Sulfosuccinate | — | 25 | 50 | 75 | 100 |

A model formula of the blends was used, in the following proportions:

| Surfactant Blend | 7.2% active |
|---|---|
| Cocamide DEA | 5.0% |
| Sodium Chloride | 2.0% |
| Water qs. to | 100.0% |
| pH = | 7.0 ± 0.2 |

Tests were performed using the cylinder rotation method, in the presence of 2% castor oil. The foam height and stability results are set forth in Table 5.

TABLE 5

|   | A | B | C | D | E |
|---|---|---|---|---|---|
| Initial Height (1st run) | 420 | 460 | 500 | 360 | 275 |
| Initial Height (2nd run) | 430 | 475 | 500 | 375 | 275 |
| Average | 425 | 467.5 | 500 | 367.5 | 272.5 |
| Height after 5 minutes (1st run) | 410 | 455 | 500 | 360 | 275 |
| Height after 5 minutes (2nd run) | 420 | 470 | 500 | 375 | 270 |

This data indicates that disodium dimethicone copolyol sulfosuccinate improves the foam height of the high foaming surfactant at certain concentrations and improves foam stability at all concentrations when blended with the sodium laureth-3 sulfate.

The foaming properties of disodium dimethicone copolyol sulfosuccinate were also compared with those of cocoamphocarboxyglycinate, the known surfactant used in baby shampoo formulations. The following samples were prepared and evaluated by the Ross-Miles foam test:

|   | A | B |
|---|---|---|
|   | (% active) | |
| Cocoamphocarboxyglycinate - SLES (35%) | 7.2 | — |
| Disodium Dimethicone Copolyol Sulfosuccinate - SLES (35%) | — | 7.2 |
| Cocamide DEA | 5.0 | 5.0 |
| Water, qs to | 100 | 100 |
| pH = 7.0 + 0.2 | | |
| Temperature = 25° C. | | |

The foam height results are set forth in Table 6.

TABLE 6

|   | A | B |
|---|---|---|
| Initial Height (1st run) | 130 | 130 |
| Initial Height (2nd run) | 130 | 130 |
| Height after 5 minutes | 120 | 125 |

While the foam enhancing properties of both surfactant-SLES blends are similar, the disodium dimethicone copolyol sulfosuccinate shows an improvement in height stability properties, as well as a significant reduction in eye irritation as demonstrated by the irritation studies. Such results indicate that the compositions of the present invention, dimethicone copolyol sulfosuccinates, provide surfactants with improved properties in comparison to known surfactants used for the same general purposes.

Another test comparing the foaming properties of the composition of the present invention with the active ingredients of a well known baby shampoo formulation, demonstrated more significant results than the test above. The following samples were prepared and evaluated using the Ross-Miles foam test:

|   | A | B | C | D |
|---|---|---|---|---|
|   |   |   |   | % Active |
| Disodium Dimethicone Copolyol Sulfosuccinate - SLES (50%) | 0.2 | — | 0 5 | — |
| Baby Shampoo | — | 0.2 | — | 0.5 |

The foam height results are as follows:

|   | A | B | C | D |
|---|---|---|---|---|
| Initial Height (1st run) | 145 | 95 | 170 | 135 |
| Initial Height (2nd run) | 145 | 90 | 170 | 130 |
| Average | 145 | 92.5 | 170 | 132.5 |
| Height after 5 minutes | 140 | 70 | 165 | 100 |

Comparing the results of this test, the sulfosuccinate-SLES blend shows significant improvement in foaming performance and stability over the commercial baby shampoo formulation. The results of the foam tests, when examined in conjunction with the eye irritation tests, demonstrate the improved mildness and foaming properties of the compositions of the present invention.

Another test was conducted comparing the foaming properties of various dimethicone copolyol sulfosuccinates of the present invention. Samples of 40% active solutions of the compounds were diluted to produce 1% active solutions, of the following compounds:

|   | A | B | C | D |
|---|---|---|---|---|
|   |   |   |   | % Active |
| Disodium Dimethicone Copolyol Sulfosuccinate | 1.0 | — | — | — |
| Diammonium Dimethicone Copolyol Sulfosuccinate | — | 1.0 | — | — |
| Dipotassium Dimethicone Copolyol Sulfosuccinate | — | — | 1.0 | — |
| Triethanolamine Dimethicone Copolyol Sulfosuccinate | — | — | — | 1.0 |

Tests were performed using the cylinder rotation method, in the presence of 2% castor oil. The foam height and stability results are set forth in Table 7.

TABLE 7

|   | A | B | C | D |
|---|---|---|---|---|
| Initial Height (1st run) | 275 | 285 | 250 | 260 |
| Initial Height (2nd run) | 275 | 295 | 260 | 264 |
| Initial Height (3rd run) | — | 290 | 255 | 270 |
| Average | 275 | 290 | 255 | 264 |
| Average Height after 5 Mins. | 270 | 250 | 220 | 230 |

The results of this test show that the foam enhancing and stabilizing properties of the compounds tested vary slightly, but all fall within an allowable range of values. Such results indicate improved foaming properties over those compounds currently used for the same purposes.

Finally, to determine the conditioning properties of the compounds of the present invention, a series of half-head studies (application of different shampoos to the right and left halves of test participants' heads) was conducted using a 50/50 blend of disodium dimethicone copolyol sulfosuccinate and sodium laureth-3 sulfate as one test sample and a well known baby shampoo as the other. In comparison with the baby shampoo, the sulfosuccinate-SLES blend exhibited improved properties in detangling, wet and dry combing, smoothness, fullness and body of the hair treated. The sulfosuccinate-SLES blend demonstrated properties equal to the baby shampoo in foam performance as well as distribution and rinsability times. Flash foaming for the baby shampoo was slightly better in volume and stability than the sulfosuccinate-SLES blend, but the overall test results demonstrate that the sulfosuccinates of the present invention provide improved surfactants over those known and used in the industry.

It should be understood, of course, that the compositions described above are intended to illustrate embodiments of the invention and do not limit the scope of the invention, which is defined by the claims set forth below. It should also be understood that alternatives to and equivalents of the specific embodiments described can be made and indeed are contemplated without departing from the scope of the invention as defined in the claims set forth below.

What is claimed is:

1. A surfactant for use in personal care products having low irritating properties and improved foaming properties comprising a blend of a silicone-based sulfosuccinate and a relatively irritating high-foaming surfactant, wherein the sulfosuccinate is selected from the group consisting essentially of compounds of the formula

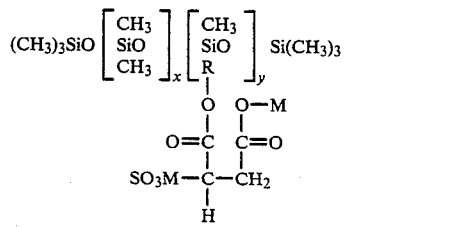

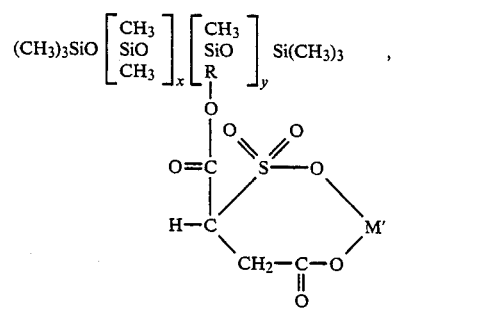

and mixtures thereof, wherein R is a polymer or copolymer of ethylene or propylene oxide, M is an alkali metal or ammonium group, M' is an alkaline earth metal or ammonium group, X is an amine group obtained from an alcohol amine, ethoxylate or propoxylate and x and y range in value so as to produce a compound with an equivalent weight between 700 and 1600 grams.

2. The surfactant of claim 1 wherein the blend comprises at least about 25% silicone-based sulfosuccinate and a balance of the relatively irritating high-foaming surfactant.

3. The surfactant of claim 1 wherein the blend comprises at least about 50% silicone-based sulfosuccinate a balance of the relatively irritating high-foaming surfactant.

4. The surfactant of claim 1 wherein the blend comprises at least about 75% silicone-based surfactant and a balance of the relatively irritating high-foaming surfactant.

5. The surfactant of claim 1 wherein the relatively irritating high-foaming surfactant consists of sodium laureth-3 sulfate.

6. The surfactant of claim 2 wherein the relatively irritating high-foaming surfactant consists of sodium laureth-3 sulfate.

7. The surfactant of claim 3 wherein the relatively irritating high-foaming surfactant consists of sodium laureth-3 sulfate.

8. The surfactant of claim 4 wherein the relatively irritating high-foaming surfactant consists of sodium laureth-3 sulfate.

9. A surfactant for use in personal care products having improved conditioning properties comprising at least about 50% silicone-based sulfosuccinate and a balance of a relatively irritating high-foaming surfactant, wherein the sulfosuccinate is selected from the group consisting essentially of compounds of the formula

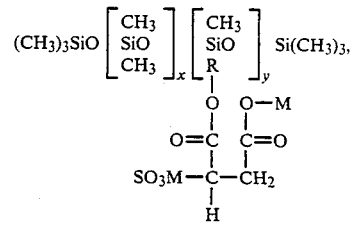

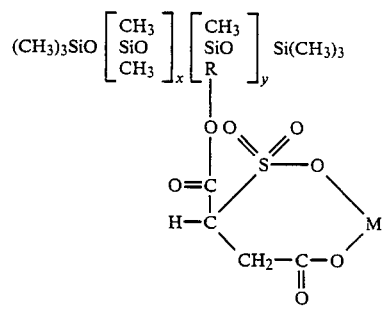

and mixtures thereof, wherein R is a polymer or copolymer of ethylene or propylene oxide, M is an alkali metal or ammonium group, M' is an alkaline earth metal or ammonium group, X is an amine group obtained from an alcohol amine, ethoxylate or propoxylate and x and y range in value so as to produce a compound with an equivalent weight between 700 and 1600 grams.

10. The surfactant of claim 9 wherein the relatively irritating high-foaming surfactant consists of sodium laureth-3 sulfate.

11. A surfactant having improved foamability properties comprising of a blend of at least about 25% to about 75% silicone-based surfactant and a balance of a relatively high-foaming surfactant, wherein the sulfosuccinate is selected from the group consisting essentially of compounds of the formula

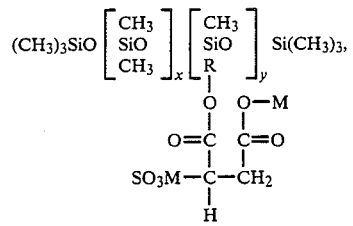

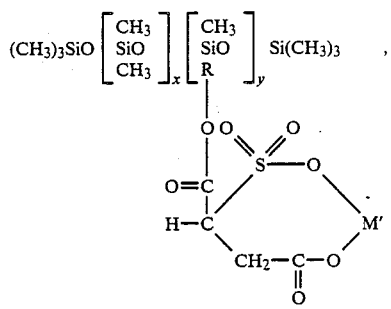

and mixtures thereof, wherein R is a polymer or copolymer of ethylene or propylene oxide, M is an alkali metal or ammonium group, M' is an alkaline earth metal or ammonium group, X is an amine group obtained from an alcohol amine, ethoxylate or propoxylate and x and y range in value so as to produce a compound with an equivalent weight between 700 and 1600 grams.

12. The surfactant of claim 11 wherein the relatively irritating high-foaming surfactant consists of sodium laureth-3 sulfate.

13. A method of producing a blended surfactant comprising the steps of
reacting dimethicone copolyol with maleic anhydride to form a monoester, and
sulfonating the monoester with a compound selected from the group consisting of alkaline sulfite, alkali sulfite, ammonium sulfite, amine sulfite or a combination of alkaline, alkali or ammonium sulfites and an amine to form a silicone-based sulfosuccinate, wherein the sulfosuccinate is selected from the group consisting essentially of compounds of the formula

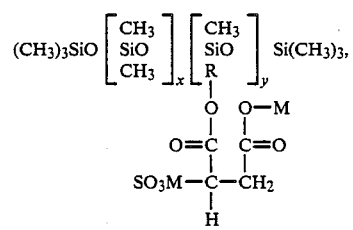

-continued

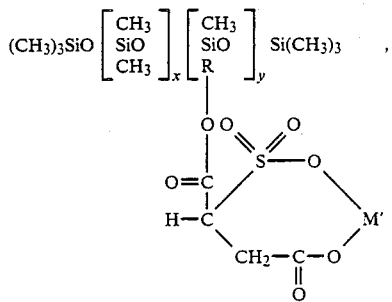

and mixtures thereof, wherein R is a polymer or copolymer of ethylene or propylene oxide, M is an alkali metal or ammonium group, M' is an alkaline earth metal or ammonium group, X is an amine group obtained from an alcohol amine, ethoxylate or propoxylate and x and y range in value so as to produce a compound with an equivalent weight between 700 and 1600 grams;
and blending a slicone-based sulfosuccinate with a relatively irritating high-foaming surfactant.

14. The method of claim 13 wherein the surfactants are blended to provide a blend comprising at least about 25% silicone-based surfactant.

15. The method of claim 13 wherein the surfactants are blended to provide a blend comprising at least about 50% silicone-based surfactant.

16. The method of claim 13 wherein the surfactants are blended to provide a blend comprising at least about 75% silicone-based surfactant.

17. The surfactant of claim 1 wherein R is selected from the group consisting essentially of:

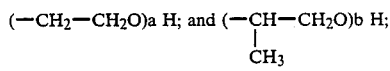

wherein a and b range in value from 1 to 30;

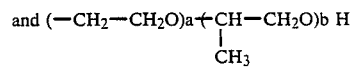

wherein a and b range in value from 0 to 30.

18. The surfactant of claim 1 wherein x and y are determined by the ratio of x and y to R, such ratio having a value of 1.5:1 to 15.3:1.

19. The surfactant of claim 1 wherein the ratio of x and y to R has a value of 10:1 to 15.3:1.

20. The surfactant of claim 9 wherein R is selected from the group consisting essentially of:

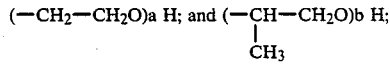

wherein a and b range in value from 1 to 30;

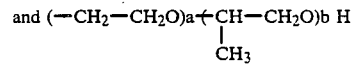

wherein a and b range in value from 0 to 30.

21. The surfactant of claim 9 wherein x and y are determined by the ratio of x and y to R, such ratio having a value of 1.5:1 to 15.3:1.

22. The surfactant of claim 9 wherein the ratio of x and y to R has a value of 10:1 to 15.3:1.

23. The surfactant of claim 11 wherein R is selected from the group consisting essentially of:

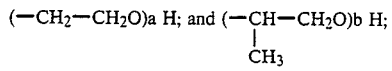

wherein a and b range in value from 1 to 30;

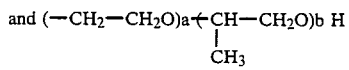

wherein a and b range in value from 0 to 30.

24. The surfactant of claim 11 wherein x and y are determined by the ratio of x and y to R, such ratio having a value of 1.5:1 to 15.3:1.

25. The surfactant of claim 11 wherein the ratio of x and y to R has a value of 10:1 to 15.3:1.

26. The method of claim 13 wherein R is selected from the group consisting essentially of:

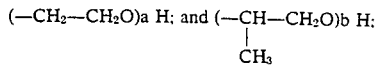

wherein a and b range in value from 1 to 30;

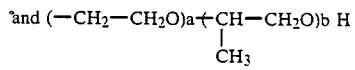

wherein a and b range in value from 0 to 30.

27. The method of claim 13 wherein x and y are determined by the ratio of x and y to R, such ratio having a value of 1.5:1 to 15.3:1.

28. The method of claim 13 wherein the ratio of x and y to R has a value of 10:1 to 15.3:1.

* * * * *